United States Patent [19]

Graham

[11] Patent Number: 4,784,122

[45] Date of Patent: Nov. 15, 1988

[54] PORTABLE CERVICAL TRACTION DEVICE USING CONSTANT FORCE SPRINGS

[76] Inventor: Erwin W. Graham, 59 Quail Hollow Dr., San Jose, Calif. 95128

[21] Appl. No.: 896,946

[22] Filed: Aug. 15, 1986

Related U.S. Application Data

[63] Continuation-in-part of Ser. No. 662,333, Oct. 17, 1984, Pat. No. 4,606,333, which is a continuation-in-part of Ser. No. 585,361, Mar. 1, 1984, Pat. No. 4,593,684.

[51] Int. Cl.[4] .......... A61F 5/04

[52] U.S. Cl. .......... 128/75; 128/84 C

[58] Field of Search .......... 128/75, 84 R, 84 C

[56] References Cited

U.S. PATENT DOCUMENTS

| | | | |
|---|---|---|---|
| 833,987 | 10/1906 | Truslow | 5/440 |
| 1,747,174 | 2/1930 | Knowles | 128/71 |
| 2,282,653 | 5/1942 | Herzmark | 128/84 C |
| 2,581,802 | 1/1952 | Lyons | 155/174 |
| 3,046,980 | 7/1962 | Moore et al. | 128/75 |
| 3,124,126 | 3/1964 | Spinks | 128/71 |
| 3,683,900 | 8/1972 | Alessi et al. | 128/84 C |
| 3,888,243 | 6/1975 | Powlan | 128/75 |
| 3,960,145 | 6/1976 | Scarbrough | 128/68.1 |
| 4,166,459 | 9/1979 | Nightingale | 128/75 |
| 4,483,330 | 11/1984 | Jacobson et al. | 128/75 |
| 4,508,109 | 5/1985 | Saunders | 128/75 |
| 4,538,598 | 9/1985 | Gill et al. | 128/75 |

FOREIGN PATENT DOCUMENTS

| | | | |
|---|---|---|---|
| 1020154 | 11/1957 | Fed. Rep. of Germany | 128/78 |
| 2355848 | 5/1974 | Fed. Rep. of Germany | 128/71 |
| 3037619 | 5/1982 | Fed. Rep. of Germany | 128/75 |
| 2290184 | 11/1974 | France | 128/75 |

*Primary Examiner*—Edgar S. Burr
*Assistant Examiner*—Tonya Lamb

[57] ABSTRACT

A compact cervical traction apparatus having a carriage which is slidably disposed over a base, the carriage carrying a head support band. A pair of springs that provide a uniform traction force over the entire range of carriage movement are enclosed within a spring housing at the rear of the base. The springs are constant force springs and an uncoiled portion of the first spring is disposed below an uncoiled portion of the second spring. The uncoiled portion of the first spring is attached to a Z-shaped member having an elongated trailing end that is mounted to the carriage so as to bias the carriage. The uncoiled portion of the second spring is attached to a lip member that is disposed to securely fit within the Z-shaped member and thereby combine the traction force of the second spring to that of the first spring. An L-shaped disengaging plate has a portion which passes between the uncoiled portions of the springs proximate attachment of the lip member to the Z-shaped member. The disengaging plate also has a cam surface portion. Pressure applied to the cam surface portion causes the disengaging portion of the plate to separate the lip member and the Z-shaped member sufficiently to prevent coupling. Such pressure is selectively supplied by a cam pivotably secured to the spring housing. The constant force springs each provide a traction force of four pounds to the carriage.

8 Claims, 3 Drawing Sheets

PORTABLE CERVICAL TRACTION DEVICE USING CONSTANT FORCE SPRINGS

CROSS REFERENCE TO RELATED APPLICATIONS

This application is a continuation-in-part of application Ser. No. 662,333, filed Oct. 17, 1984, now U.S. Pat. No. 4,606,333 which is a continuation-in-part of Ser. No. 585,361, filed Mar. 1, 1984, now U.S. Pat. No. 4,593,684.

TECHNICAL FIELD

The invention relates to a portable traction device.

BACKGROUND ART

Vertebral problems of the cervical spine sometimes require the relief of excessive intervertebral pressure. Traction is required to elongate the cervical spine to release this pressure. The most commonly used method is to have the patient seated with a neck or chin strap to which tension is applied through a rope over a pulley with a weight attached. The chin strap stresses the temporomandibular joint with possible pain and deformity of the joint. The chin strap immobilizes the jaw and prevents talking. Since the head weighs approximately ten pounds, this weight must be exceeded before any effective elongation of the cervical section can take place.

Other procedures employ straps which are wrapped around the head at the occipital area and also use a forehead strap to hold the head. The pressure of tension across the forehead and temple require more elaborate harness straps. A chin and head strap require auxiliary suspension points, such as a door.

Traction devices for a reclining patient are known. U.S. Pat. No. 4,593,684 to applicant discloses a portable traction device which engages the occipital region of the back of the skull. U.S. Pat. No. 4,166,459 discloses a traction device which uses a sliding carriage with a raised preshaped yoke which engages the neck. An elastically biased carriage holding the yoke applies force. The unit must be attached to a mattress for anchoring.

An object of the present invention is to devise a portable cervical traction apparatus which is self-contained and used without support equipment, such as a door. Another object of the invention is to devise such an apparatus which provides a force that remains the same even after a change of positioning by the subject.

DISCLOSURE OF THE INVENTION

The objects have been met by a compact cervical traction unit which provides a constant force over its entire range of movement. The construction includes a horizontal base having a forwardly disposed movable carriage on which is mounted a brace that supports a flexible band for engaging the occipital region of the skull. A pair of springs provide a force to the movable carriage.

A first constant force spring is coiled atop the rear portion of the horizontal base. The axis of the coil extends perpendicularly to the plane of carriage movement. An opening in the base accepts a free end of the first constant force spring so that the free end may be braced under the base and toward the front portion of the base for attachment to the carriage. A second constant force spring is mounted directly in front of the first spring, whereby a free end of the second spring may pass through an opening in the base and then toward the carriage, directly atop the uncoiled portion of the first constant force spring. A lip member attached to the free end of the second constant force spring is disposed to be selectively secured to a Z-shaped member attached to the free end of the first spring. When the lip member is attached to the Z-shaped member, the combined force of the springs is applied to the carriage. Preferably, the springs each provide a constant force of four pounds. The range of carriage movement may be as great as three feet.

An L-shaped disengaging plate has a cam surface portion that extends parallel the plane of carriage movement, adjacent the constant force springs. The disengaging plate further has a disengaging portion which passes between the uncoiled portion of the springs proximate the attachment of the lip member to the Z-shaped member. A pivoting cam member is disposed atop the rear portion of the carriage to apply force to the cam surface portion of plate, pressing the disengaging portion downward to separate the lip member from the Z-shaped member, thereby releasing the carriage from biasing contact with the second constant force spring.

Additional constant force springs may be applied to the assembly and selectively attached to the carriage in the same manner as the second constant force spring. While it is not necessary that additional springs have a force of four pounds, it has been discovered that the four pound increments supplied by the first and second springs are advantageous and, in actuality, supply the only forces necessary in the treatment of the majority of vertabral problems of the cervical spine.

BEST MODE FOR CARRYING OUT THE INVENTION

Figure 1:
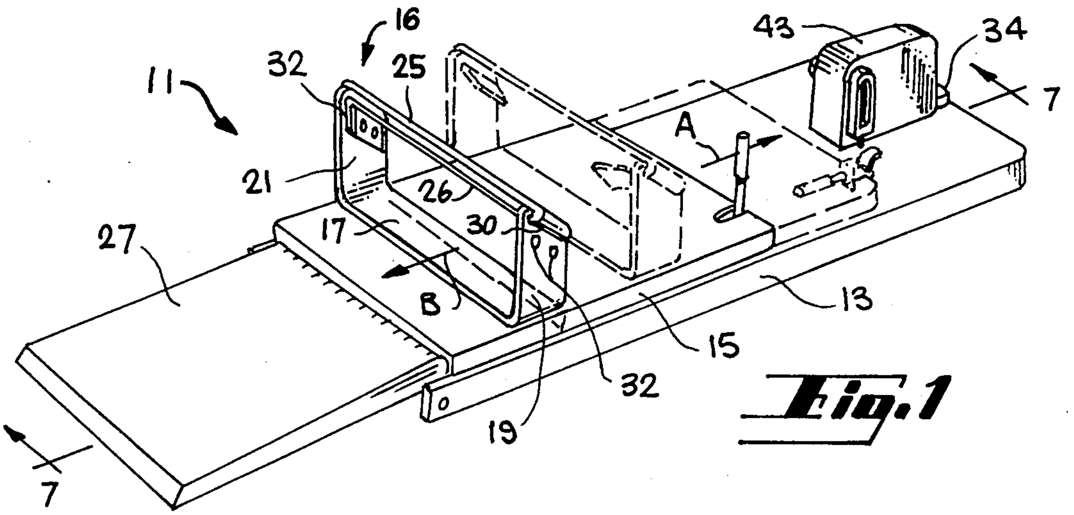
FIG. 1 is a perspective front view of the cervical traction apparatus of the present invention.

With reference to FIG. 1, cervical traction apparatus 11 has a flat elongated base 13 that is horizontally disposed. The base has dimensions of approximately 20 inches long, seven and one-half inches wide, and one-half inch deep. A carriage 15 with dimensions ten inches long and seven and one-half inches in width is mounted so as to move horizontally back and forth just over the base in the directions of arrows A and B.

Mounted near the forward end of the carriage 15 is a head cradle assembly 16 consisting of a metal brace 17 having two upwardly extending side arms 19 and 21 with a head supporting band 25 connected therebetween. The side arms are about three inches high and about seven and one-half inches apart from each other, and have the taut, wide flexible band 25 anchored through narrow slots 30 in each side arm and fastened by screws 32. The side arms of the brace are of a trapezoid shape. Due to the angle of the slots 30, the band 25 lies in a tilted position at an angle between 30° and 60° from the horizontal, thereby facing toward the rear of carriage 15. The band has a thickness of approximately three-sixteenths inches and a width of two inches. The head supporting band is made of a resilient elastomeric material such as silicone rubber and has an optimum durometer measurement of 45–55*d* which flexes to fit to the shape of the occipital area of the skull when the back of the head is placed in the head support. An elastic strap 26 is disposed beneath band 25 for added support.

Figure 2:
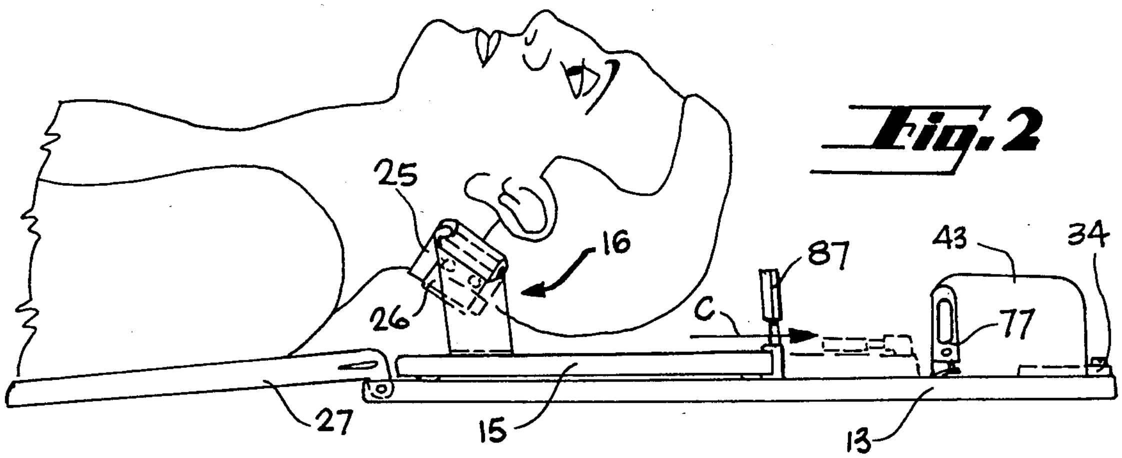
FIG. 2 is a side view of the apparatus of FIG. 1 showing the apparatus in use.

Operation of the cervical traction apparatus of the present invention may best be understood with reference to FIG. 2. The neck of a user is lowered toward the elastomeric band 25. On contact with the band, the band begins to fold and shape itself to the natural lordotic curve. Then, as the neck is lowered to full contact and traction is applied in the direction of arrow C, the effect of the downward weight of the neck and the pull of the traction is to apply pressure on the lower side of the occipital bone. This permits the traction effect along the entire cervical spine. The band is thus in a position to be securly seated and can act as a fulcrum. The head can be tipped forward or backward as needed to work with the user's normal lordotic curve, without losing the secure position on the band.

The force which is applied to the head causes the supporting unit to move forward. This is overcome in the invention by an anchor pad 27. During traction a reclining patient's back rests on the anchor pad which may be made of foam on metal covered with durable material, similar to a thin canvas pillow. The anchor pad is approximately the same width as the base 13 and may be of varying lengths but, preferably, the pad is shorter than the base to permit it to be folded under the base. The entire apparatus, when folded, may be compactly stored and suspended from hanger 34.

Figure 3:
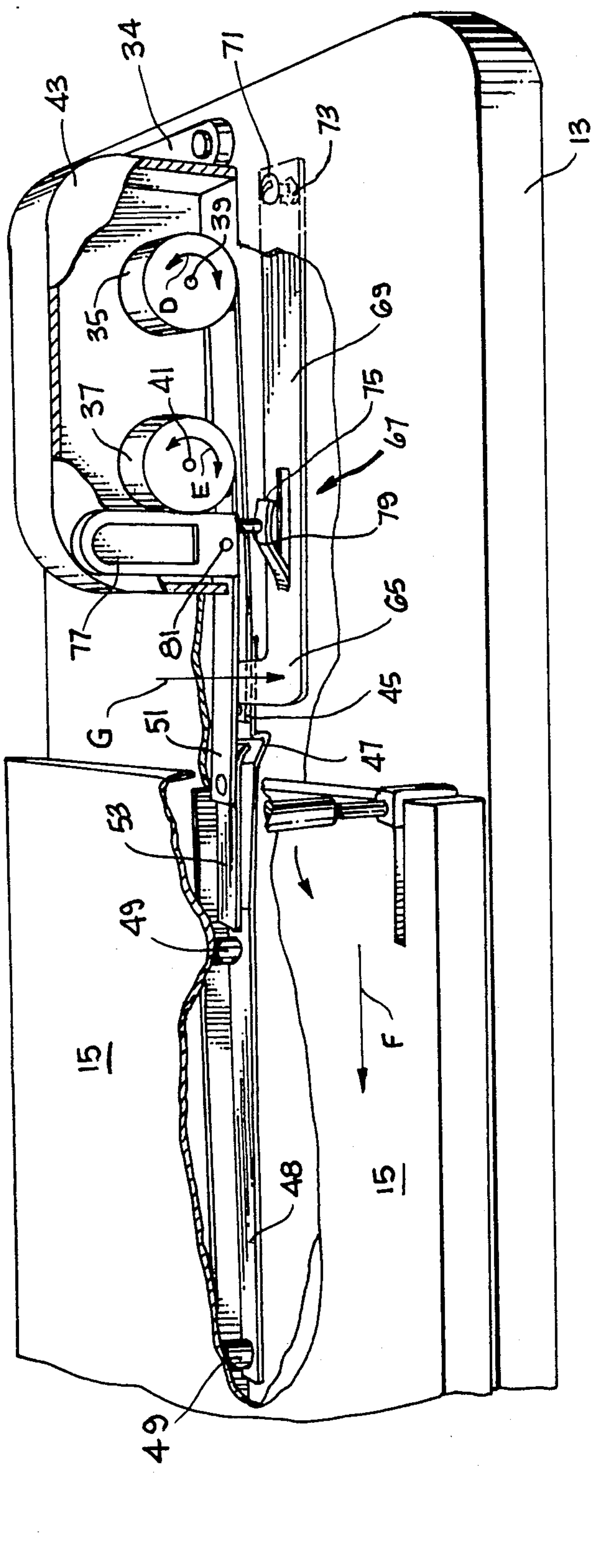
FIG. 3 is a partial cutaway view of the spring assembly of FIG. 1.

With reference to FIG. 3 traction forces are applied to move the carriage 15 by means of a spring system having two constant force springs 35, 37. Constant force springs 35, 37 are each coiled about an axis 39, 41, as shown by arrows D and E. The coils are enclosed within a housing 43 and are constructed to provide a constant force of four pounds each over the entire range of carriage movement. The constant force springs may be obtained from Walker Spring Co. of Sante Fe Springs, Calif.

Typically, springs obey Hook's Law. That is, as a spring is extended, the spring will exert an increasingly greater force to return to a relaxed position. Constant force springs, on the other hand, exert a uniform force irrespective of the amount of spring extension. A user of the present invention may therefore periodically stretch the neck or make slight changes in body position without concern of increasing or decreasing the traction force.

FIG. 3 illustrates the traction apparatus having only the first constant force spring 35 providing traction force to the carriage 15. The free end 45 of the first spring passes through an opening in the portion of the base below the spring. The free end is attached to a Z-shaped member 47. The Z-shaped member has an elongated trailing end 48 that is mounted to the carriage 15. Spacers 49 distance the Z-shaped member from the carriage. As the carriage is moved in the direction indicated by arrow F, the first spring 35 provides a constant traction force of four pounds to the head cradle assembly.

Figure 4:
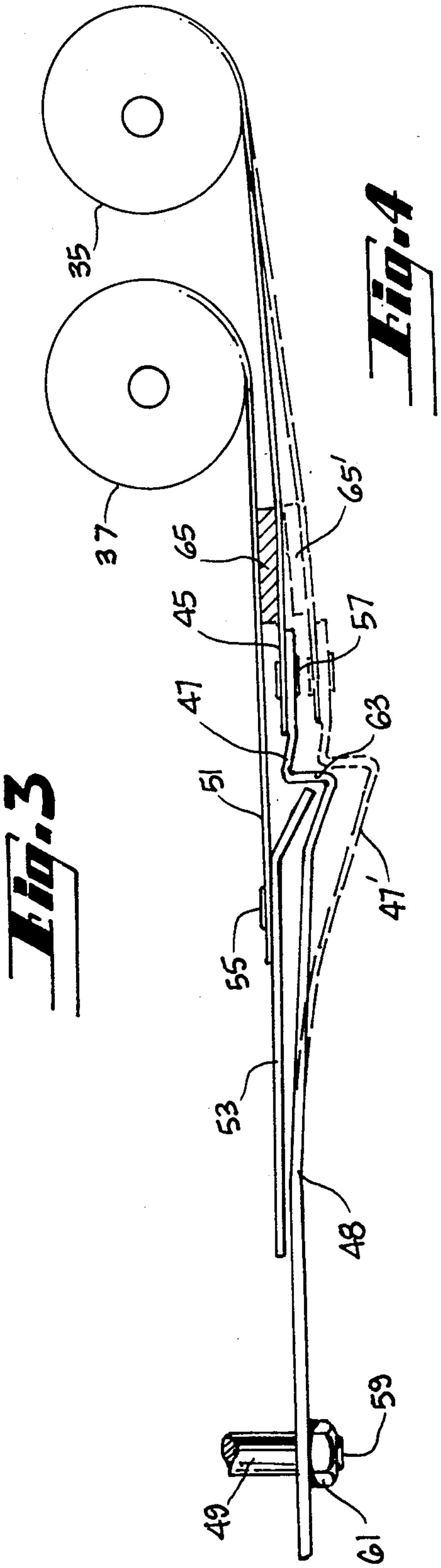
FIG. 4 is a side view of the spring assembly of FIG. 4.

The second constant force spring 37 also has a force of four pounds and this force may be added to that of the first spring 35. The second spring has a free end 51 which is attached to a lip member 53. FIG. 4 best illustrates the construction and the interaction of the lip member 53 and the Z-shaped member 47. The lip member is attached to the free end 51 of the second spring by a rivet 55. Likewise, the Z-shaped member is mounted to the first spring by means of a rivet 57 or a spot weld. The elongated trailing end 48 of the Z-shaped member is held to the spacer 49 and the carriage by a screw 59 and nut 61 arrangement. The lip member is aligned to abut the vertical portion 63 of the Z-shaped member and to make contact with the elongated trailing end 48 when the carriage is moved in the direction of arrow F of FIG. 3. In this manner the combined force of the two springs is applied to the carriage.

As can be seen in FIGS. 3 and 4, a disengaging portion 65 of a L-shaped disengaging plate 67 passes between the free ends 45, 51 of the springs. The disengaging plate 67 has a cam surface portion 69 that is secured to the base 13 by a screw 71 and nut 73 arrangement. The cam surface portion has a separation that is ramped upward to form a cam surface 75. Downward pressure, indicated by arrow G, on the disengaging plate 67 will place the disengaging portion into a lowered position 65'. As a result, the Z-shaped member 47' is situated so that it will not make contact with the lip member 53. That is, the second constant force spring 37 will not be in biasing contact with the carriage when the disengaging plate portion is in position 65'.

The disengaging plate 67 is forced downward by a cam 77 having a projection 79. The cam is pivotally mounted to the spring housing 43 at pivot point 81. When the cam is oriented vertically the cam projection 79 forces the ramped cam surface 75 downward, thereby causing the misalignment of the lip member 53 with respect to the Z-shaped member 47'.

Figure 5:
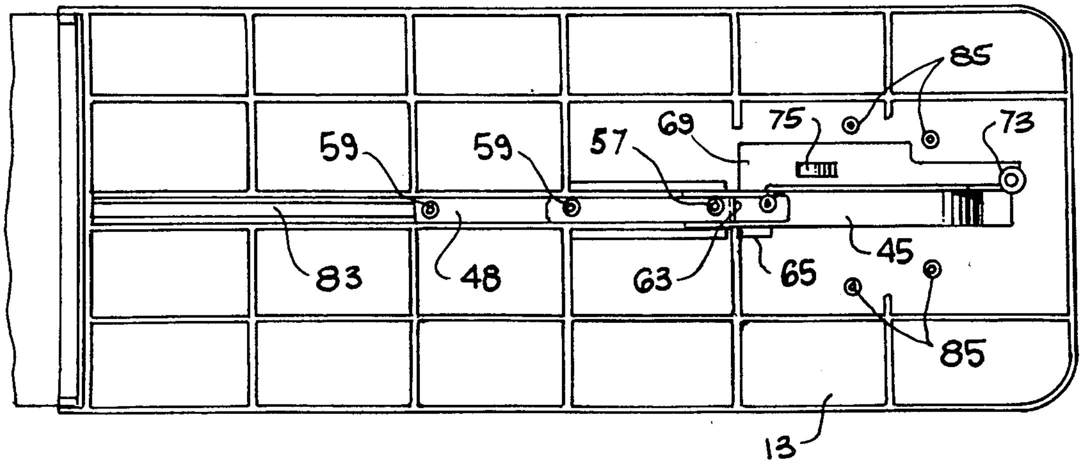
FIG. 5 is a bottom view of the apparatus of FIG. 1.

FIG. 5 is a bottom view of the base 13. The base contains a channel 83 that is suffcently wide to permit horizontal movement of the carriage without interference from the screws 59 or spacers, not shown, that retain the elongated trailing end 48 of the Z-shaped member to the carriage. The free end 45 of the first spring provides a constant force of four pounds to the carriage. Screws 85 secure the spring housing to the base.

Figure 6:
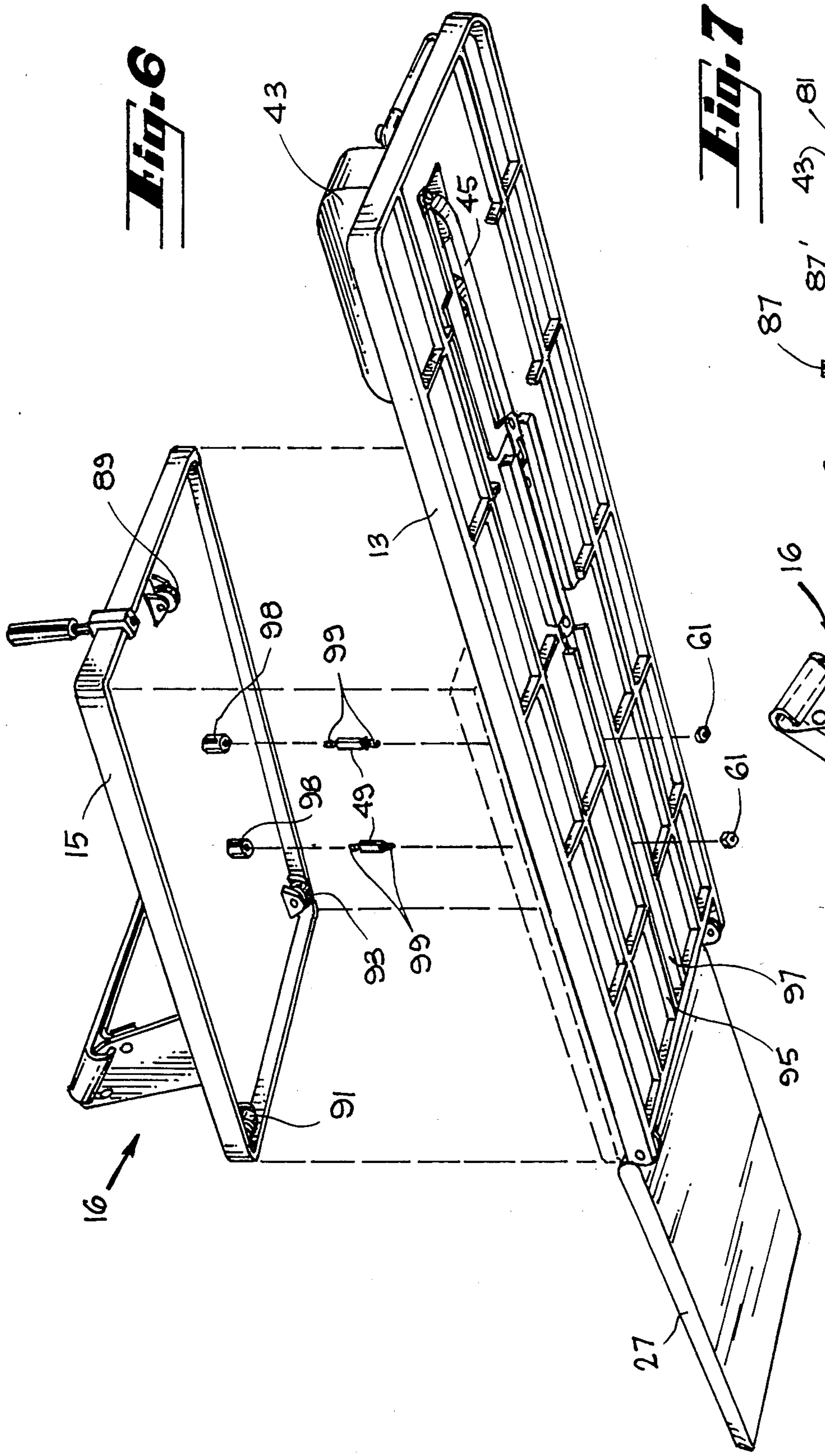
FIG. 6 is an exploded perspective view of the cervical traction device of FIG. 1.

As shown in FIG. 6, carriage 15 rides on the surface of base 13 by means of three wheels 89, 91, and 93. Wheel 89 is set under the middle of the rear of carriage 15 and wheels 91 and 93 are set under opposite corners of the carriage front. Both the base and the carriage are formed with downturned edges which serve to protect the wheels under the carriage. The channel 83 is defined between two parallel protective rails 95, 97 which extend lengthwise along the midline of the bottom surface of the base. Spacers 49 run in the channel 83 and contact posts 98. Washers 99 are disposed on each side of the spacers 49. By this means the carriage is slideably mounted on the base.

Figure 7:
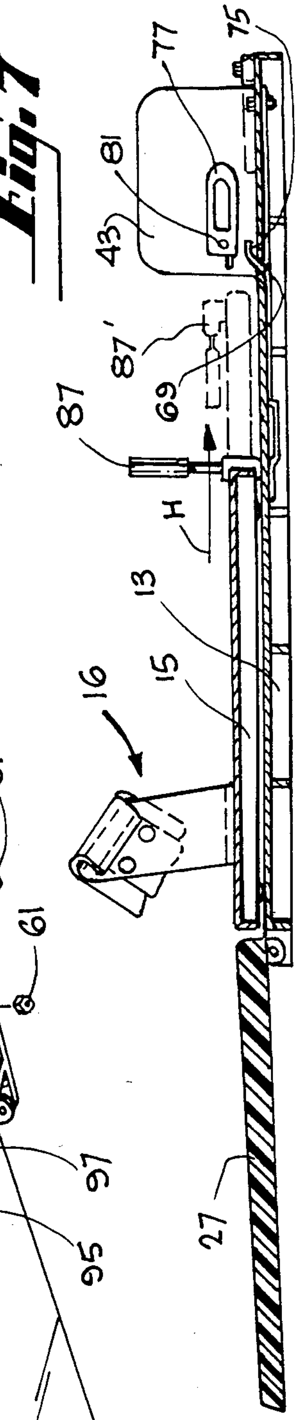
FIG. 7 is a cross-sectional view of the apparatus taken along lines 7—7 of FIG. 1.

In operation, FIG. 7 shows that the apparatus has a locking mechanism 87 that secures the carriage 15 in a position furthermost from the spring housing 43. When the head of the user is comfortably postioned, the user disengages the pivotal locking mechanism from a receptacle mounted on the base. In position 87' the carriage is free to slide so that the force from the springs provide traction force to the head cradle assembly 16 in the direction of arrow H.

Both springs will be in biasing contact with the carriage when the cam 77 is in a horizontal position. In this position the cam is out of contact with the cam surface 75 leaving the disengaging plate 67 high, thereby aligning the Z-shaped member 47 for contact with the lip member 53. The lip member will be engaged by the Z-shaped member when the carriage is moved away from the spring housing 43.

Only the first constant force spring will be in biasing contact with the carriage when the cam is pivoted into a vertical position. With the cam in a vertical position the disengaging plate is held low by the projection 79 of the cam. The disengaging plate will thus hold the Z-shaped member below the lip member, preventing the second constant force spring from combining with the first spring to provide traction force to the carriage.

The illustrated arrangement shows utilization of only two constant force springs. Additional constant force springs may be employed. However, the two springs, each furnishing four pounds of force, are sufficient for the treatment of the majority of vertebral problems of the cervical spine. The uniform force of the springs over the entire range of carriage movement is critical. The constant force springs permit a patient to periodically change positions or stretch muscles without unintentionally varying the traction force. The arrangement adds to the comfort and safety of the apparatus.

The entire unit weighs approximately three pounds. The base and carriage may be molded from a plastic such as an ABS resin. These are light weight, have good impact strength, and are dimensionally stable and resistant to most oils and chemicals. The brace for the head cradle may be steel, aluminum or plastic. The head band should preferably be a hypo-allergenic material such as a silicone rubber of a thickness to give a good support to the occipital area.

I claim:

1. A portable cervical spine traction apparatus comprising, a flat elongated support base adapted to be horizontally disposed and having front and rear portions, a carriage slideably mounted on the front portion of said base, said carriage having a means for engaging the back of the skull, and a spring means for biasing said carriage rearwardly relative to said support base, said spring means mounted to the rear portion of said base and having a first and a second constant force spring, connectable together for increasing bias by predetermined amounts of force, said first constant force spring being attached to said carriage and said second constant force spring being selectively engaged to said first constant force spring, and release means for disengaging said second constant force spring from said first constant force spring, said release means having a cam and a disengaging plate, said disengaging plate having a cam surface portion and a portion passing between said constant force springs, said cam capable of exerting force on said disengaging plate, thereby separating said second constant force spring from said first constant force spring.

2. The apparatus of claim 1 wherein said second constant force spring has a lip member and said first constant force spring has a Z-shaped member to selectively lock said second constant force spring to said first constant force spring.

3. The apparatus of claim 1 wherein each constant force spring provides a four pound force to bias said carriage rearwardly.

4. The apparatus of claim 1 wherein said means for engaging the back of the skull includes a resilient elastomeric support band for engaging the occipital region by elastomeric flexing.

5. A portable cervical spine traction apparatus comprising, a planar support base having a planar carriage mounted for slideable motion thereon and means for limiting the relative motion of the base and carriage to linear motion, a head support mounted to the carriage, biasing means for providing a uniform biasing force over the entire range of carriage motion, said biasing means including first and second constant force springs mounted to said support base, said constant force springs each coiled about an axis extending perpendicularly to said motion of the carriage, each spring having an uncoiled portion, said constant force springs aligned so that said uncoiled portion of said first constant force spring is parallel to and directly below said uncoiled portion of the second constant force spring, at least one constant force spring being attached to said carriage, and locking means for selectively locking said uncoiled portions of said springs to each other, said locking means including a lip member and a z-shaped member, said z-shaped member attached to the uncoiled portion of said first spring, said lip member attached to the uncoiled portion of the second spring and disposed to engage the z-shaped member, said means for selectively locking said uncoiled portions further including a means for selectively separating said lip member and said z-shaped member.

6. The apparatus of claim 5 wherein said means for selectively separating said lip member from said z-shaped member includes a cam and a disengaging plate, said disengaging plate having a cam surface portion and a disengaging portion, said disengaging portion extending between said uncoiled portions of said springs, said cam capable of exerting force on said cam surface portion, thereby spacing apart said uncoiled portions.

7. The apparatus of claim 5 wherein each constant force spring provides a four pound force to bias said carriage.

8. The apparatus of claim 5 wherein said head support includes a rigid brace having two upwardly extending arms supporting a resilient elastomeric band for engaging the occipital region of the skull.

* * * * *